United States Patent [19]

Hendricks et al.

[11] Patent Number: 5,738,850
[45] Date of Patent: Apr. 14, 1998

[54] THERAPEUTIC COMPOSITION FOR THE TREATMENT OF SKIN LESIONS AND METHODS FOR ITS PREPARATION

[76] Inventors: Horst Walter Hendricks; Sabine Hendricks, both of Weseler Str. 20, D-47169 Duisburg, Germany

[21] Appl. No.: 750,137
[22] PCT Filed: May 17, 1995
[86] PCT No.: PCT/EP95/01884
 § 371 Date: Feb. 10, 1997
 § 102(e) Date: Feb. 10, 1997
[87] PCT Pub. No.: WO95/32723
 PCT Pub. Date: Dec. 7, 1995

[30] Foreign Application Priority Data

May 31, 1994 [DE] Germany ............ 44 18 976.1

[51] Int. Cl.$^6$ .................................. A61K 35/78
[52] U.S. Cl. ............... 424/195.1; 514/934; 514/925; 514/861; 514/886
[58] Field of Search ............... 424/195.1; 514/934, 514/925, 861, 886

[56] References Cited

U.S. PATENT DOCUMENTS 4,469,685 9/1984 Kojima et al. .............. 424/195.1
5,061,491 10/1991 Deryabin ................... 424/195.1

FOREIGN PATENT DOCUMENTS 1792050 10/1971 Germany .............. A61K 35/78

OTHER PUBLICATIONS

The New England Journal of Medecine, 303, No. 10, 583 (Jul. 3, 1980).

*Primary Examiner*—Jean C. Witz
*Attorney, Agent, or Firm*—Anderson, Kill & Olick, P.C.

[57] ABSTRACT

The invention relates to a phytotherapeutic agent for the treatment of skin lesions and morbid skin changes. In particular, it should be suitable for functioning as an effective therapeutic agent for the treatment of herpes simplex without significant side effects.

The phytotherapeutic agent consists of an extract of components extractable from sage, (*Salvia officinalis*), ribwort plantain (*Plantago lanceolata*), greater plantain (*Plantago major*) and mistletoe (*Viscum album*).

6 Claims, No Drawings

5,738,850

THERAPEUTIC COMPOSITION FOR THE TREATMENT OF SKIN LESIONS AND METHODS FOR ITS PREPARATION

FIELD OF INVENTION

The invention relates to a phytotherapeutic agent for the treatment of skin lesions and morbid changes in the skin and methods for its preparation.

BACKGROUND INFORMATION AND PRIOR ART

It is well known that herpes simplex is a pantropic, facultative neurotropic virus disease due to a primary infection with herpes simplex viruses (HSV 1 or 2) or by reactivating viruses persisting in ganglia. The incubation time in the case of a primary infection is 2 to 7 days; transmission: after the maternal antibody protection has subsided, the first infections occurs mostly in young children due to smear and droplet infections from herpes lesions or from healthy permanent carriers. A herpes infection does not confer lifelong immunity. Relapses can occur due to irritation of latent infected neurons after feverish infections, isolation, menstruation, traumas and gastrointestinal disorders, but also due to immunosuppression and hormonal or physical factors. The symptoms are itching and a sensation of tenseness, then grouped vesicles on a reddened background, which dry out to crusts and heal without scars after 8 to 10 days; regional lymph nodes frequently are slightly swollen and painful. Herpes simplex can recur at regular intervals, possibly also always at the same site. The location usually is in the region of the lips, the vulva or the penis and also in the face.

The presently known therapeutic agents and remedies have some disadvantages; this is true for the known organic or inorganic chemotherapeutic agents, as well as for the known phytotherapeutic agents. Creams, gels, solutions and powders are offered, some of which contain plant components, such as extracts of balm leaves, echinacea, chamomile, arnica, etc. or pharmaceutically active organic chemicals, such as benzocaine, sulfonamides, tetracaine, allantoin, vidarabin, acyclovir, ribavivirin, didesoxycytidine, azidothymidine or inorganic chemicals, such as elemental sulfur, insoluble mercury salts and soluble mercury salts in homeopathic concentrations.

The known phytotherapeutic agents have only a slight healing action and are limited to an accompanying effect of the self-healing. Some of the chemotherapeutic agents have considerable side effects on cells, which are not infected, and frequently are the cause of allergic reactions. In addition, their frequent use produces mutants, so that, after some time, the chemotherapeutic agent loses its main effect and is left only with the unwanted, harmful side effects. For example, the agents, which contain acyclovir as active ingredient, must be discontinued after a 10-day use.

No agent can prevent re-infections or relapses. In view of the possibility of a herpes encephalitis infection, this is particularly serious. Most agents contain preservatives, which are also cytotoxic for eukaryotes. For this reason, latent viruses, which are present as provirus in the host cell, are provoked to reproduce the virus actively. The infection is intensified. Very few of the agents ameliorate pain; only those agents, which contain local anesthetics, such as benzocaine, form an exception. The cosmetic effect of known agents generally is very disadvantageous.

OBJECT OF THE INVENTION

The basic object of the invention therefore is to make available a therapeutic agent against herpes simplex, the main therapeutic effect of which is comparatively more pronounced. At the same time, unwanted side effects are to be minimal and negligible. Moreover, the therapeutic agent shall ameliorate pain, itching and a sensation of tenseness, resulting from the herpes simplex, and be cosmetically unobtrusive. Furthermore, it is an object of the invention to make available a therapeutic agent, which is generally suitable for the treatment of skin lesions and morbid skin changes.

SUMMARY OF THE INVENTION

Pursuant to the invention, this objective is accomplished with a phytotherapeutic agent of claim 1.

It has turned out that a topical treatment of the vesicles, which occur as a result of the infection, as well as of the adjacent tissue, by applying the inventive phytotherapeutic agent, has a uniquely good success. The application should be repeated as soon as a sensation of tenseness arises. When the inventive phytotherapeutic agent is used, the herpes heals completely within 1 to 3 days. The usual, thick incrustation of the herpes vesicles does not take place. After the disintegration of the vesicles, only an extremely thin crust, which becomes detached automatically after a short time, is deposited on the affected site. The inventive phytotherapeutic agent, applied as a liquid, is not visible and therefore also of great advantage cosmetically. The inventive phytotherapeutic agent can be used until there no longer are any incrustations.

The action of the inventive phytotherapeutic agent apparently takes place in the connective tissue. It is conceivable that the active substances, present in the combination described, interact synergistically, in that, on the one hand, weakened cells, infected by viruses, are killed and destroyed, as a result of which the potential of the virus to reproduce is limited and, on the other, the defense and healing powers of the healthy parts of the tissue are reinforced or supplemented directly or indirectly. Direct vitality impairment of viruses by contact with the phytotherapeutic agent has been proven experimentally.

The inventive phytotherapeutic agent is particularly suitable for the treatment of lesions of the skin and outer mucous membrane, such as the treatment of infections by the herpes simplex virus (types 1 and 2), of the varicella zoster virus and of the papilloma virus. The inventive phytotherapeutic agent can also be administered orally, by injection or by infusion, for example, for the treatment of a herpes encephalitis infection. It has also been observed that the inventive phytotherapeutic agent is suitable for the treatment of neurodermatitis, mycosis fungoides and weeping eczemas, as well as for the treatment of gastritis and for the treatment of stomach cramps.

It is known that mistletoe contains numerous substances, which can act as methylating agents. As a result of general investigations, it appears that at least one of these has the ability to methylate selectively genes, which code for replication. A portion of the zytostatic activity of mistletoe is attributable to this ability. However, a cell has demethylation enzymes, the function of which is mainly to demethylate methylated genes of transcriptionally silent chromosomes, if the corresponding genes of the homologous chromosomes no longer are capable of functioning. Since the expression of the cell's own replication genes is essential for mitosis, these genes are demethylated once again and the cytostatic ability, based on the ability described, is only slight. On the other hand, it is conceivable that the viral replication genes are not required and therefore are also not demethylated. They remain repressed and the virus can no longer synthesize all the components, which are required for replication. However, since not all of the genes of the provirus are repressed, the provirus synthesizes vital enzymes. All enzymes of the cell, that is, the cell's own enzymes as well as viral enzymes, are now and then chopped up routinely by special enzymes to peptides, in order to represent the peptides of killer T cells. Since the virus no longer is able to reproduce actively, the immune system has more time to react to the infection. Basically, killer T cells are able to recognize viral peptides as foreign and to kill an infected cell. These specific killer T cells evidently reproduce preferentially continuously and thus contribute very appreciably to a rapid healing of the vesicles and to an effective protection against reinfections and relapses. It has been observed that, even in persons specially so predisposed, herpes infections occur constantly less frequently in the course of about 4 years, until they finally they remain absent altogether.

Of the active ingredients of mistletoe, only the viscotoxins and lectins have been researched in depth. It is known that mistletoe lectin I or its sugar-bonding sub-unit, which is referred to as the B chain, links specifically to lymphocytes and precursors of macrophages and stimulates these to excrete various substances, capable of modulating the immune response, such as the tumor necrosis factor and interleukins 1 and 6. As a result, the activity of the killer T cells is increased. The sub-unit of the mistletoe lectin I, referred to as A chain, inhibits the synthesis of proteins within the cell. Viscotoxins damage the cell membrane. Administered individually, the two substances or classes of substances quite generally damage healthy, infected and degenerated cells equally. In combination with the numerous other active substances, they apparently act selectively on infected and degenerated cells.

Aside from the direct damage to preferably infected and degenerated cells, other, more indirect mechanisms of action are also possible. A mode of action is conceivable, for which the active substances, such as lectins, are deposited selectively on the surfaces of infected and degenerated cells. These cells thus become recognizable to the immune system as foreign. A mechanism of action is also conceivable, which consists therein that active substances, such as polysaccharides, coincidentally have structure characteristics similar to those occurring on the surfaces of infected or degenerated cells and that these structure characteristics of the active substances are recognized as foreign by the immune system and provoke a reaction. After this reaction, the immune system can then also recognize the structure characteristics on the surface of infected or degenerated cells as foreign. This means that the structure characteristics on the surfaces of infected and degenerated cells must stand between the body's own unobtrusive structure characteristics and the structure characteristics of the active substances.

Some of the mistletoe substances have a compensating effect on the central nervous system and act spasmolytically. As a result, the patient presumably no longer has any itching, burning or pain.

The known indications of the sage, such as night sweat, excessive perspiration, diseases of the spinal cord, liver dysfunctions, lung, kidney and bladder atony, as well as inflammations of the mucous membrane of the mouth and throat, lead one to believe that there are numerous and versatile active substances. Inflammation-inhibiting, astringent and bactericidal substances are known.

In the phytotherapy literature, the greater plantain has previously been dealt with only together with the ribwort. However, it has been noted that the proportion of greater plantain in the inventive phytotherapeutic agent is of essential importance and cannot, under any circumstances, be replaced by a higher proportion of ribwort. The known indications of the ribwort and greater plantain are catarrh of the respiratory passages, liver, kidney and bladder diseases, hemorrhoids, lymphatic vessel disorders, inflammatory changes in the mucous membrane of the mouth and the throat, gangrenous wounds, purulent abscesses and dermatoses. Here also, numerous and versatile active substances are suspected. The outstanding active antibiotic substance of ribwort and greater plantain are known. Admittedly, the content is not so high that these materials can compete with penicillin or modern antibiotics from fungi. However, it is sufficient for guaranteeing that the shelf life of the inventive phytotherapeutic agents is about six months, when these agents are kept at a temperature not greater than 8° C. With only a slight loss of effectiveness, the shelf life of the inventive phytotherapeutic agent can also be extended to a period of more than one year by the addition of natural preservatives, such as vitamin C.

All of the plants, required for producing the inventive phytotherapeutic agent, contain numerous ingredients, which have not yet been researched and, in some cases, not yet clarified. These include further active substances. Possible reactions and structural changes of the ingredients, particularly during an increase in temperature resulting from the extraction, cannot be presented comprehensively at the present time. Neither can the number of possible interactions, synergisms or antagonisms. According to previous healing results, it is not possible to do without either of the plants. The composition could at best be supplemented for symptomatic treatment by further plants, such as hawthorn (*Crataegus monogyna*) or garlic (*Allium sativum*). The individual active substances of the four plants supplement, harmonize with and reinforce one another in such a manner that their overall effect so far can be understood only as a whole.

Since the inventive phytotherapeutic agent is composed of "Mite Pharmaka", which represent defined natural materials, are monographed and registered with the Bundesgesundheitsamt (Federal Department of Health) in the DAB 8 (German Pharmacopoeia, 8th edition), intolerable toxic side effects are not to be expected. According to previous applications, unwanted side effects cannot be ascribed to the inventive phytotherapeutic agent. Moreover, it could be used as often and for as long as necessary, without the occurrence of resistant mutants being noticed.

The healing potential of the inventive phytotherapeutic agent for various virus infections has been described above. For example, it was observed that warts, after a 10-day treatment with the inventive phytotherapeutic agent, had already receded to such an extent, that they are visible now only as a small collection of pigments. The mechanisms of action of the inventive phytotherapeutic agent in the case of neoplasms are presently still largely unknown (possible mechanisms were already described above). However, it seems that mistletoe substances (in collaboration with the extracts of the remaining plants) can eliminate weakened cells (malignant, degenerated cells). Furthermore, these substances appear to sensitize the immune system to malignant, degenerated cells. The effectiveness of the inventive phytotherapeutic agent for treating bacterial infections and mycoses appears to be based primarily on the mobilization of the immune system (as described above) and on an immunogenic identification of the exogenous material.

For preparing the inventive phytotherapeutic agent, particularly the methods, which are described in claims 3 to 6 and differ according to the intended use, are suitable.

In an advantageous method for extracting the active substances out of the plants, the latter are boiled with pure drinking water or distilled water. Boiling water is a good solvent for the active substances and heat kills the vegetative cells of bacteria and fungi or yeasts. Boiling once usually ensures adequate preservation for weeks and months. Among other things, the boiling up evidently brings about a coagulation of toxic mistletoe proteins, whereas the desirable proteins go into colloidal solution. If mild toxic side reactions can be tolerated, the extraction can also be carried out at room temperature. It is possible to accelerate the dissolving process, for example, by boiling under vacuum or using an approximately 3% to 7% by weight solution of salt or sea salt. For the facultative treatment of persistent or resistant infections and neoplasms, the active substances can also be extracted from the plants or from the residue of aqueous extractions with lipophilic solvents, preferably with food oils, butter or margarine.

The invention is described in greater detail below by means of a special non-limiting example.

The dried leaves (10 g) of sage (*Salvia officinalis*), 15 g of dried plant parts of ribwort (*Plantago lanceolata*), 15 g of dried plant parts of greater plantain (*Plantago major*) and 25 g of dried plant parts of mistletoe (*Viscum album*) were added to 1000 mL of lukewarm drinking water or distilled water, slowly brought to the boil and boiled for about 3 minutes with mild heating. The extraction mixture was allowed to cool and then filtered after about 3 hours.

The filtrate can be adjusted to the desired electrolyte or non-electrolyte concentration by evaporation or the addition of sea salt and distilled water. This is done advantageously by the use of semi-permeable membranes and adjusted solutions.

The filtrate must previously be sterilized carefully, if it is to be applied as an injection or an infusion. Sterilization can be accomplished, for example, by microfiltration.

We claim:

1. A therapeutic composition for the treatment of skin lesions consisting of an effective amount of extracts of sage, ribwort plantain, greater plantain and mistletoe, and either a water-soluble preservative or a fat-soluble preservative.

2. The therapeutic composition of claim 1, wherein the composition contains 5 to 50 g of sage, 5 to 100 g of ribwort plantain, 5 to 100 g of greater plantain, and 10 to 200 of mistletoe per liter of an extraction solvent.

3. The therapeutic composition of claim 2, wherein the composition contains 10 g of sage, 15 g of ribwart plantain, 15 g of greater plantain, and 25 g of mistletoe per liter of an extraction solvent.

4. A method of preparation of a therapeutic composition consisting of an effective amount of extracts of sage, ribwort plantain, greater plantain and mistletoe, and either a water-soluble preservative or a fat-soluble preservative, said method comprising the steps of:

extracting the dried components of sage, ribwort plantain, greater plantain and mistletoe in a hydrophilic or lipophilic extraction solvent or in an extraction solvent acting as a surfactant; and adding either a water-soluble preservative or a fat-soluble preservative.

5. The method of claim 4, wherein said extracting step includes using water which has a temperature of about 80° C.+110° C. during the extraction of 60 to 300 sec as the extraction solvent.

6. The method of claim 4, wherein said extracting step includes using a 3% to 7% by weight solution of salt or sea salt which is heated during the extraction to about 40° C. as the extraction solvent.

* * * * *